US012797320B2

(12) United States Patent
Saji et al.

(10) Patent No.: US 12,797,320 B2
(45) Date of Patent: Nov. 17, 2026

(54) ORGANIC COMPOUNDS

(71) Applicant: Givaudan SA, Vernier (CH)

(72) Inventors: Norikazu Saji, Chartham Canterbury (GB); Nicolas Cocito Armanino, Baden (CH); Jonathan Richards, Kennington Ashford (GB)

(73) Assignee: GIVAUDAN SA, Vernier (CH)

( * ) Notice: Subject to any disclaimer, the term of this patent is extended or adjusted under 35 U.S.C. 154(b) by 399 days.

(21) Appl. No.: 18/279,872

(22) PCT Filed: Mar. 8, 2022

(86) PCT No.: PCT/EP2022/055802

§ 371 (c)(1),
(2) Date: Aug. 31, 2023

(87) PCT Pub. No.: WO2022/189383

PCT Pub. Date: Sep. 15, 2022

(65) Prior Publication Data

US 2024/0165004 A1 May 23, 2024

(30) Foreign Application Priority Data

Mar. 8, 2021 (GB) ...................................... 2103207

(51) Int. Cl.
*A61K 8/49* (2006.01)
*A61K 8/34* (2006.01)
*A61Q 11/00* (2006.01)

(52) U.S. Cl.
CPC ................ *A61K 8/498* (2013.01); *A61K 8/34* (2013.01); *A61Q 11/00* (2013.01); *A61K 2800/92* (2013.01)

(58) Field of Classification Search
CPC ........ A61K 8/34; A61K 8/4946; A61K 8/498; A61K 2800/92; A61Q 11/00
See application file for complete search history.

(56) References Cited

U.S. PATENT DOCUMENTS

| | | | | |
|---|---|---|---|---|
| 7,414,152 | B2 * | 8/2008 | Galopin | C07C 255/44<br>558/414 |
| 2007/0059417 | A1 | 3/2007 | Moza et al. | |
| 2010/0048589 | A1 | 2/2010 | Colburn et al. | |
| 2015/0139918 | A1 | 5/2015 | Ages et al. | |

FOREIGN PATENT DOCUMENTS

| | | | |
|---|---|---|---|
| EP | 1121927 | A2 | 8/2001 |
| WO | 9517156 | A1 | 6/1995 |
| WO | 2017151589 | A1 | 9/2017 |
| WO | 2021074281 | A1 | 4/2021 |
| WO | 2022028726 | A1 | 2/2022 |

OTHER PUBLICATIONS

Lachenmeier et al., What happens if people start drinking mouthwash as surrogate alcohol? A quantitative risk assessment, Food and Chemical Toxicology, 51 (2013) 173-178. (Year: 2013).*
John C. Leffingwell, “Cool without Menthol & Cooler than Menthol and Cooling Compounds as Insect Repellants”, Internet Citation, pp. 1-19, 2010.
International Search Report for PCT Application No. PCT/EP2022/055802, dated Jul. 21, 2022.
International Written Opinion for PCT Application No. PCT/EP2022/055802, dated Jul. 21, 2022.
Great Britain Search Report for Application No. GB2103207.3, dated Aug. 27, 2021.

* cited by examiner

*Primary Examiner* — Lezah Roberts
(74) *Attorney, Agent, or Firm* — Curatolo Sidoti & Trillis Co., LPA; Floyd Trillis, III; Salvatore A. Sidoti

(57) ABSTRACT

Provided are compositions possessing an enhanced alcoholic taste impression.

12 Claims, 1 Drawing Sheet

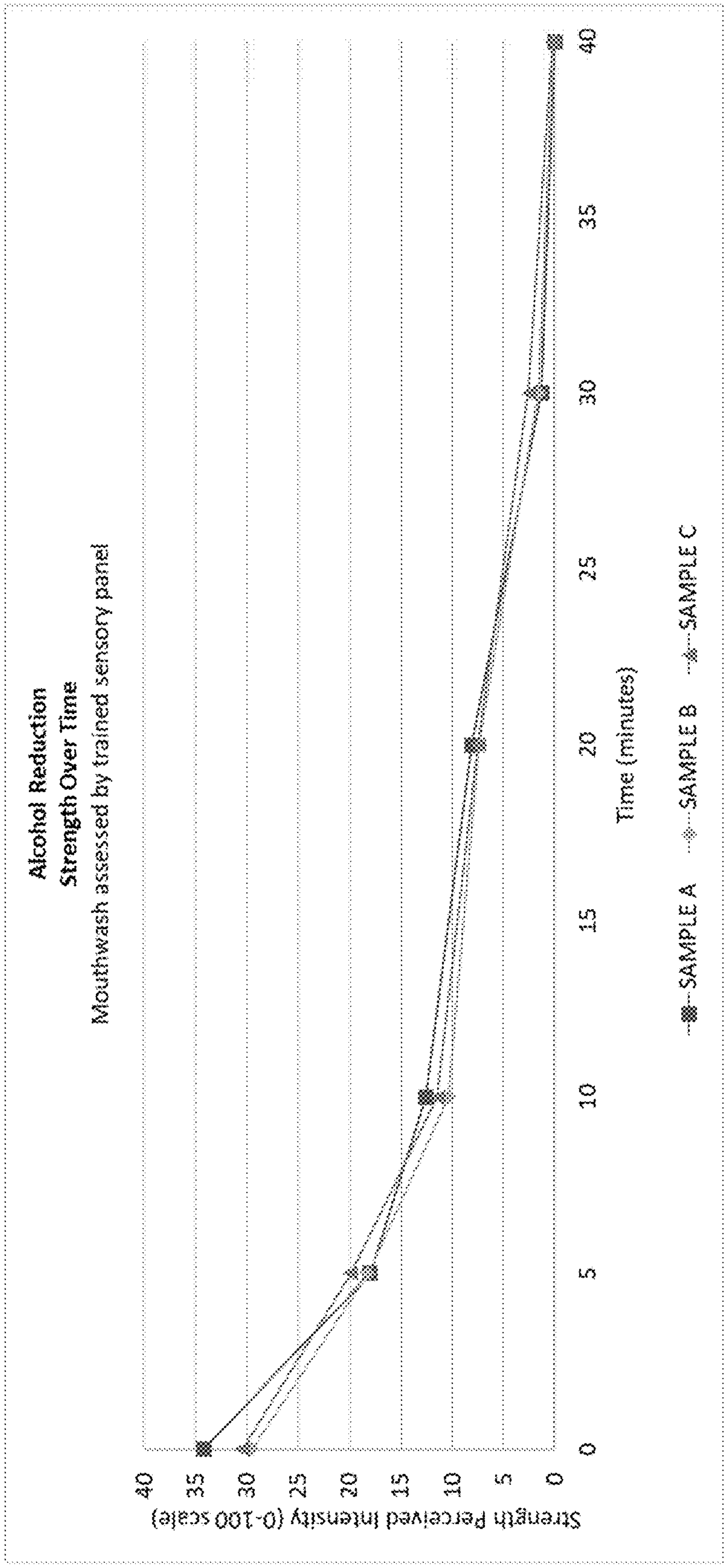
Alcohol Reduction
Strength Over Time
Mouthwash assessed by trained sensory panel
Strength Perceived Intensity (0-100 scale)
40
35
30
25
20
15
10
5
0
Time (minutes)
0
5
10
15
20
25
30
35
40
SAMPLE A
SAMPLE B
SAMPLE C

ORGANIC COMPOUNDS

CROSS REFERENCE TO RELATED APPLICATIONS

This application is a national stage application of International Application No. PCT/EP2022/055802, filed 8 Mar. 2022, which claims priority from Great Britain Application No. 2103207.3, filed 8 Mar. 2021, both of which applications are incorporated herein by reference.

TECHNICAL FIELD

The present invention generally relates to liquid compositions possessing an enhanced alcoholic taste impression. There is further provided a method of enhancing the alcoholic taste of an orally perceived composition, in particular mouthwash compositions, and the use of certain compounds to enhance the alcoholic taste in said orally received compositions.

BACKGROUND

Alcohol mouthwash is a popular product globally and some consumers like the intensity and burn impressions caused by liquid oral care products comprising higher amounts of alcohol. The standard products on the marked comprise approximately 20% ethanol. However, there are growing health concerns about such high alcohol formulations. Thus, there is an increasing demand for products comprising no alcohol or at least products with less amounts of alcohol. Unfortunately such products tend to lack the intense alcoholic character.

Compounds that can enhance the taste of alcohol are of great interest and may allow not only to enhance the alcohol taste but also to reach a certain taste intensity at a reduced concentration of alcohol (ethanol). For example, without limitation, in alcoholic compositions having a low ethanol concentration but still provide the same or very similar taste as their non-reduced counterparts.

The applicant has now found that, by the addition to an alcoholic liquid compositions, e.g. oral care composition and alcoholic beverages, of a non-natural cooling compound, the alcoholic taste is enhanced, thus less alcohol is required to achieve an essentially similar intensity of the alcoholic character compared to their non-reduced counterparts.

SUMMARY OF THE INVENTION

In accordance with a first aspect of the present invention there is provided a method of enhancing in an alcoholic liquid composition the taste sensations associated with alcohol, comprising adding to said product a non-natural cooling compound.

In one particular embodiment the non-natural cooling compound is selected from the list consisting of I) a compound of formula (I), a salt or solvate thereof (I)

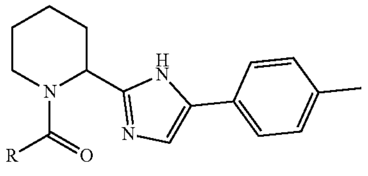

wherein R is an $C_3$-$C_7$ branched alkyl or alkenyl optionally comprising one S atom;

II) N-substituted para-menthane carboxamides of formula (II)

(II)

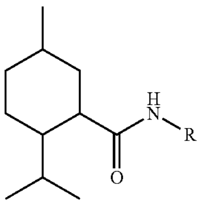

wherein R is selected from substituted phenyl (e.g. 4-(cyanomethyl)phenyl, 4-methoxyphenyl), $C_2$-$C_4$ alkyl (e.g. ethyl, tert-butyl), (pyrdinyl)alkyl (e.g, 2-(pyridin-2-yl) ethyl), and —$CH_2$—C(O)—O—$C_2H_5$, or mixtures thereof.

In one particular embodiment the alcoholic liquid composition is an oral care product, such as mouthwash, including concentrated mouthwash, or mouth spray.

In accordance with a second aspect of the present invention there is provided an alcoholic liquid compositions, e.g. oral care composition, comprising a) a non-natural cooling compound; and b) at least 1 vol. % ethanol.

In one particular embodiment the non-natural cooling compound is selected from the group consisting of the compounds as listed for the first embodiment.

BRIEF DESCRIPTION OF THE FIGURES

FIG. 1 shows the perceive intensity of an alcoholic mouthwash over time. The alcoholic mouthwash samples comprising 20 weight %, 10 weight % and 5 weight % ethanol (96 v/v).

DETAILED DESCRIPTION

The present invention is based, at least in part, on the surprising finding that non-natural cooling compounds enhance the alcoholic taste of an orally perceived liquid composition, for example, oral care compositions such as mouthwash products, including mouth spray products.

Thus, there is provided in a first aspect a method of enhancing in an alcoholic liquid composition, e.g. oral care compositions, the taste sensations associated with alcohol, comprising adding to said product a non-natural cooling compound.

In one particular embodiment the non-natural cooling compound is selected from the group consisting of I) a compound of formula (I), a salt or solvate thereof (I)

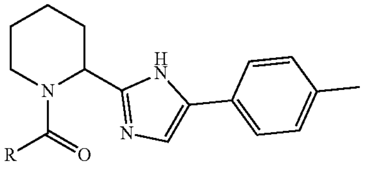

wherein R is an $C_3$-$C_7$ branched alkyl or alkenyl optionally comprising one S atom; and II) N-substituted para-menthane carboxamides of formula (II)

(II)

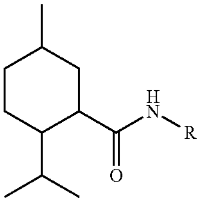

wherein R is selected from substituted phenyl (e.g. 4-(cyanomethyl)phenyl, or 4-methoxyphenyl), $C_2$-$C_4$ alkyl (e.g. ethyl, or tert-butyl), (pyrdinyl)alkyl (e.g, 2-(pyridin-2-yl) ethyl), and —$CH_2$—C(O)—O—$C_2H_5$.

The compounds of formula (I) comprise several chiral centers and as such exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis. The compounds as defined by formula (I) may exist in its tautomeric forms 1H-Imidazole-3H-Imidazole form. Accordingly, the chemical structures depicted herein encompass all possible sterioisomers and tautomeric forms of the illustrated compounds.

The compounds of formula (I) can be generally prepared as described in the international patent application PCT/EP2020/079009 (WO 2021/074281) which is incorporated by reference.

Non-limiting examples are compounds of formula (I) wherein R is $C_4$-$C_5$ branched alkyl or alkenyl, e.g., R is but-2-yl or 2-methyl-but-3-en-2-yl.

Further non-limiting examples are compound of formula (I) wherein R is $C_3$-$C_4$ branched alkyl comprising one S atom, e.g., R is 2-methyl-3-thiabut-2-yl or 3-thiabut-2-yl.

The compounds of formula (I) selected from the group consisting of 2-methyl-1-(2-(5-(p-tolyl)-1H-imidazol-2-yl) piperidin-1-yl)butan-1-one (including (2S)-2-methyl-1-(2-(5-(p-tolyl)-1H-imidazol-2-yl)piperidin-1-yl)butan-1-one, and (2R)-2-methyl-1-(2-(5-(p-tolyl)-1H-imidazol-2-yl)piperidin-1-yl)butan-1-one), 2-(methylthio)-1-(2-(5-(p-tolyl)-1H-imidazol-2-yl)piperidin-1-yl)propan-1-one, 2-methyl-2-(methylthio)-1-(2-(5-(p-tolyl)-1H-imidazol-2-yl)piperidin-1-yl)propan-1-one, and 2,2-dimethyl-1-(2-(5-(p-tolyl)-1H-imidazol-2-yl)piperidin-1-yl)but-3-en-1-one.

Non-limiting examples of compounds of formula (II) are 2-isopropyl-5-methyl-N-(2-(pyridin-2-yl)ethyl)cyclohexane-1-carboxamide (including (1R,2S,5R)-2-isopropyl-5-methyl-N-(2-(pyridin-2-yl)ethyl)cyclohexane-1-carboxamide), N-[4-(cyanomethyl)phenyl]-(1S,2S,5R)-2-isopropyl-5-methylcyclohexanecarboxamide, N-4-methoxyphenyl-(1S,2S,5R)-2-isopropyl-5-methylcyclohexanecarboxamide, N-ethyl-(1S,2S,5R)-2-isopropyl-5-methylcyclohexane-carboxamide, N-tert-butyl-(1S,2S,5R)-2-isopropyl-5-methylcyclohexanecarboxamide, and ethyl (2-isopropyl-5-methylcyclohexane-1-carbonyl) glycinate.

In one particular embodiment the non-natural cooling compound of formula (II) is a high potency cooling compound, such as, 2-isopropyl-5-methyl-N-(2-(pyridin-2-yl) ethyl)cyclohexane-1-carboxamide (including (1R,2S,5R)-2-isopropyl-5-methyl-N-(2-(pyridin-2-yl)ethyl)cyclohexane-1-carboxamide), N-[4-(cyanomethyl)phenyl]-(1S,2S,5R)-2-isopropyl-5-methylcyclohexanecarboxamide, and N-4-methoxyphenyl-(1S,2S,5R)-2-isopropyl-5-methylcyclohexanecarboxamide The cooling potency (strength) of a compound is defined by its $EC_{50}$, value. $EC_{50}$, (half maximal effective concentration) refers to the concentration of a compound which induces a response halfway between the baseline and maximum after a specified exposure time. It is commonly used as a measure of potency. $EC_{50}$, is a measure of concentration, expressed in μM (μmolar) units, where 1 μM is equivalent to 1 μmol/L. As used in relation to the non-natural cooling compounds "high potency" refers to non-natural cooling compound which elicits an in-vitro activation of TRPM8 (transient receptor potential melastatin member 8, also known as Trp-p8 or MCR1) with an $EC_{50}$, <0.3 μM.

In another particular embodiment the non-natural cooling is a mixture, comprising a compound of formula (I) and a compound of formula (II).

As a specific example one my cite a mixture comprising 2-isopropyl-5-methyl-N-(2-(pyridin-2-yl)ethyl)cyclohexane-1-carboxamide (II) and 2-methyl-1-(2-(5-(p-tolyl)-1H-imidazol-2-yl)piperidin-1-yl)butan-1-one (I), e.g. in a ratio from about 1:1 to 10:1 (which includes a ratio of 2:1, and 5:1).

It was surprisingly found that by addition of minor amounts of a non-natural cooling compound to an alcoholic liquid composition, e.g. oral care composition, the amount of alcohol can be reduced by at least 75% without a noticeable difference in the intensity (alcoholic taste) perceived.

In accordance with a second aspect of the present invention there is provided a liquid compositions, e.g. a oral care composition, comprising a) a non-natural cooling compound; and b) at least 1 weight % ethanol.

In one particular embodiment the liquid composition comprises up to 20 weight % ethanol (e.g. about 2, 3, 4, 4.8, 5, 6, 7, 8, 9, 9.6, 10, 11, 12, 13, 15, 17, 19.2 weight % ethanol.

By "minor amounts" is meant that a noticeable effect can already be achieved by the addition of 0.2 ppm (e.g. 0.5 to 30 ppm, which includes 2, 4, 5, 6, 20 ppm) of a non-natural cooling compound to an alcoholic liquid composition, e.g. oral care composition.

In one specific embodiment the alcoholic liquid composition, e.g. oral care composition, adapted to be received orally comprises up to 300 ppm (e.g. 2, 3, 4, 5, 6, 10, 20 ppm) of a non-natural cooling compound.

The non-natural cooling compound may be selected from the group consisting of compounds of formula (I) and/or compounds of formula (II) as hereinabove described.

In one particular embodiment the alcoholic liquid composition, e.g. oral care composition, comprises 2-isopropyl-5-methyl-N-(2-(pyridin-2-yl)ethyl)cyclohexane-1-carboxamide (II) and 2-methyl-1-(2-(5-(p-tolyl)-1H-imidazol-2-yl) piperidin-1-yl)butan-1-one (I), e.g. in a ratio from about 1:1 to 10:1 (which includes a ratio of 2:1, and 5:1).

In another embodiment the alcoholic liquid composition, e.g. oral care composition, comprises from about 2-6 ppm of 2-isopropyl-5-methyl-N-(2-(pyridin-2-yl)ethyl)cyclohexane-1-carboxamide and/or 2-methyl-1-(2-(5-(p-tolyl)-1H-imidazol-2-yl)piperidin-1-yl)butan-1-one.

Liquid oral care compositions may further comprise excipients commonly used in the art, such as surfactants (cationic or anionic), chosen from, e.g., alkali or alkaline earth metal salts of alkyl sulphonic acid, fatty acid, or alkyl ether sulphate, benzalkonium chloride, alkyl pyridinium chloride or quaternary ammonium gemini surfactants, and the like; electrolyte, e.g. a chloride, sulphate, acetate, or carbonante of an alkali, alkaline earth or transition metal (for example, calcium chloride, sodium chloride, magnesium chloride, zinc sulphate, aluminium chloride or zinc acetate);

antimicrobial actives are, for example, selected from essential oils, such as thymol, eugenol, limonene, eucalyptol, and camphor or mixtures thereof, fatty acids and the methyl esters thereof, cationic oil, such as, quaternary ammonium cationic vegetable oil, cetyl pyridiniumchloride (CPC), and organic per-acids; sweetening agents; colorants; and flavours.

Examples of sweetening agents include, but are not limited to, sucrose, fructose, glucose, high fructose corn syrup, corn syrup, xylose, arabinose, rhamnose, erythritol, xylitol, mannitol, sorbitol, inositol, acesulfame potassium, aspartame, neotame, sucralose, and saccharine, and mixtures thereof; trilobatin, hesperetin dihydrochalcone glucoside, naringin dihydrochalcone, mogroside V, Luo Han Guo extract, rubusoside, rubus extract, glycyphyllin, isomogroside V, mogroside IV, siamenoside I, neomogroside, mukurozioside IIb, (+)-hernandulcin, 4β-hydroxyhernandulcin, baiyunoside, phlomisoside I, bryodulcoside, bryoside bryonoside, abrusosides A-E, cyclocarioside A, cyclocaryoside I, albiziasaponins A-E, glycyrrhizin, araboglycyrrhizin, periandrins I-V, pterocaryosides A and B, osladin, polypodosides A and B, telosmoside A8-18, phyllodulcin, huangqioside E neoastilbin, monatin, 3-acetoxy-5,7-dihydroxy-4'-methoxyflavanone, 2R,3R-(+)-3-Acetoxy-5,7,4'-trihydroxyflavanone, (2R,3R)-dihydroquercetin 3-O-acetate, dihydroquercetin 3-O-acetate 4'-methyl ether, brazzein, curculin, mabinlin, monellin, neoculin, pentadin, thaumatin, and combinations thereof. Some of the compounds listed above are known sweetness enhancers as well as sweeteners. When used as sweetness enhancers they are normally used below their sweetness detection thresholds.

Generally any flavors such as those described in "Essential guide to food additives", Third edition 2008, page 101-321 (ISBN: 978-1-905224-50-0) by Leatherhead Food International Ltd., can be used. The publication is incorporated herein by reference.

Further examples of known flavours may be found in one of the FEMA (Flavour and Extracts Manufacturers Association of the United States) publications or a compilation thereof which is available from and published by FEMA and contains all FEMA GRAS (Generally Regarded As Safe) publications from 1965 to present, eg GRAS 21 published 2003, or in Allured's Flavor and Fragrance Materials 2004, published by Allured Publishing Inc.

Examples of flavours include natural flavors, artificial flavors, spices, seasonings, and the like. Exemplary flavor ingredients include synthetic flavor oils and flavoring aromatics and/or oils, oleoresins, essences, and distillates, and a combination comprising at least one of the foregoing.

In one specific embodiment flavour is selected from anethole, menthol laevo, carvone laevo, ethyl maltol, vanillin, eucalyptol, eugenol, menthol racemic, cis-3-hexenol, linalol, mint oil (e.g. peppermint *arvensis* oil, peppermint *piperita* oil, spearmint native oil, spearmint scotch oil), corylone, ethyl butyrate, cis-3-hexenyl acetate, citral, *eucalyptus* oil, ethyl-vanillin, ginger oil, methyl salicylate, 2'-hydroxypropiophenone, ethyl acetate, methyl dihydro jasmonate, geraniol, lemon oil, iso amyl acetate, thymol, ionone beta, linalyl acetate, decanal, (±)-dihydromint lactone (3,6-dimethyl-3a,4,5,6,7,7a-hexahydro-3H-benzofuran-2-one), cis jasmone, ethyl hexanoate, melonal (2,6-dimethylhept-5-enal), citronellol, ethyl aceto acetate, vanilla, vanillin, nutmeg oil, rosemary oil, tea tree oil, and clove oil, or mixtures thereof.

The invention is now further described with reference to the following non-limiting examples. These examples are for the purpose of illustration only and it is understood that variations and modifications can be made by one skilled in the art.

Example 1: Typical Flavour for Mouthwash Formulations

| Ingredient | Parts per weight 1/100 |
|---|---|
| ANETHOLE | 5.00 |
| L-CARVONE | 3.00 |
| L-MENTHOL | 50.00 |
| ORANGE OIL | 0.80 |
| PEPPERMINT Oil MENTHOL FREE | 25.00 |
| PROPYLENE GLYCOL | 1.10 |
| SPEARMINT OIL | 15.00 |
| Ethyl Vanillin | 0.10 |
| | 100.00 |

Example 2: Mouthwash

| Ingredient | Sample A | Sample B | Sample C |
|---|---|---|---|
| Ethanol (96% v/v) | 20.0 | 10.0 | 5.0 |
| PEG 40 Hydrogenated Castor Oil | 0.3 | 0.3 | 0.3 |
| Mint flavour (Ex. 1) | 0.3 | 0.3 | 0.3 |
| Sorbitol[1)] | 12.0 | 12.0 | 12.0 |
| Saccharin[2)] | 0.2 | 0.2 | 0.2 |
| Distilled water | q.s. to 100 weight % | q.s. to 100 weight % | q.s. to 100 weight % |

[1)]Sorbitol 70% syrup

[2)]Sodium Saccharin @ 25 weight % in distilled water

All the ingredients are mixed. To Sample B and Sample C 4 ppm of a non-natural cooling compound (i.e. a mixture consisting of 2-methyl-1-(2-(5-(p-tolyl)-1H-imidazol-2-yl)piperidin-1-yl)butan-1-one and (1R,2S,5R)-2-isopropyl-5-methyl-N-(2-(pyridin-2-yl)ethyl)cyclohexane-1-carboxamide) at a ratio of 1:1) have been added.

20 ml of the mouthwash samples were swilled in the mouth for 30 seconds before expectorated. No rinse water was used. The panellists were then asked to rate on a linear scale from 0-100 the intensity (alcoholic taste) immediately after rinsing and after 5, 10, 30 and 40 minutes.

The order of samples assessed was pre-determined using a balanced randomisation (Latin Square design) to minimize any carry over or order effects. The samples were assessed in a sequential monadic format.

The results are shown in FIG. 1.

As can be seen from the chart the perceived intensity is very similar for all samples over time. The data confirm that by the addition of 4 ppm of non-natural cooling to an alcoholic liquid the amount of alcohol can be reduced by at least 75% without compromising on intensity (alcoholic taste).

The invention claimed is:

1. A liquid composition comprising a) a mixture of non-natural cooling compounds; and b) at least 1 weight % ethanol;

wherein the mixture of non-natural cooling compounds comprises:

I) a compound of formula (I), a salt or solvate thereof (I)

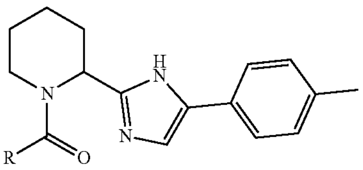

wherein R is an $C_3$-$C_7$ branched alkyl or alkenyl optionally comprising one S atom; and II) N-substituted para-menthane carboxamides of formula (II)

(II)

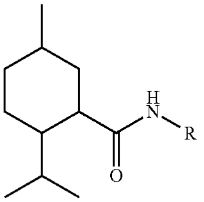

wherein R is selected from substituted phenyl, $C_2$-$C_4$ alkyl, (pyrdinyl)alkyl, $—CH_2—C(O)—O—C_2H_5$.

2. The liquid composition according to claim 1, wherein the non-natural cooling compound of formula (I) is selected from the group consisting of 2-methyl-1-(2-(5-(p-tolyl)-1H-imidazol-2-yl) piperidin-1-yl) butan-1-one, 2-(methylthio)-1-(2-(5-(p-tolyl)-1H-imidazol-2-yl) piperidin-1-yl) propan-1-one, 2-methyl-2-(methylthio)-1-(2-(5-(p-tolyl)-1H-imidazol-2-yl) piperidin-1-yl) propan-1-one, 2,2-dimethyl-1-(2-(5-(p-tolyl)-1H-imidazol-2-yl) piperidin-1-yl) but-3-en-1-one, and mixtures thereof.

3. The liquid composition according to claim 1, wherein the composition is an oral care composition.

4. The liquid composition according to claim 2, wherein the composition is an oral care composition.

5. The liquid composition according to claim 1, wherein the non-natural cooling compound of formula (II) is selected from the group consisting of 2-isopropyl-5-methyl-N-(2-(pyridin-2-yl)ethyl)cyclohexane-1-carboxamide, N-[4-(cyanomethyl)phenyl]-(1S,2S,5R)-2-isopropyl-5-methylcyclohexane-carboxamide, N-4-methoxyphenyl-(1S,2S,5R)-2-isopropyl-5-methylcyclohexanecarboxamide, N-ethyl-(1S,2S,5R)-2-isopropyl-5-methylcyclohexanecarboxamide, N-tert-butyl-(1S,2S,5R)-2-isopropyl-5-methylcyclohexanecarboxamide, ethyl (2-isopropyl-5-methylcyclohexane-1-carbonyl)glycinate, and mixtures thereof.

6. The liquid composition according to claim 5, wherein the composition is an oral care composition.

7. A method of enhancing in an alcoholic liquid composition having at least 1 weight % ethanol the taste sensations associated with alcohol, comprising adding to said composition the mixture of non-natural cooling compounds according to claim 1.

8. The method according to claim 7, wherein the compound of formula (I) is selected from the group consisting of 2-methyl-1-(2-(5-(p-tolyl)-1H-imidazol-2-yl) piperidin-1-yl) butan-1-one, 2-(methylthio)-1-(2-(5-(p-tolyl)-1H-imidazol-2-yl) piperidin-1-yl) propan-1-one, 2-methyl-2-(methylthio)-1-(2-(5-(p-tolyl)-1H-imidazol-2-yl) piperidin-1-yl) propan-1-one, 2,2-dimethyl-1-(2-(5-(p-tolyl)-1H-imidazol-2-yl) piperidin-1-yl) but-3-en-1-one, and mixtures thereof.

9. The method according to claim 7, wherein the compound of formula (II) is selected from the group consisting of 2-isopropyl-5-methyl-N-(2-(pyridin-2-yl)ethyl)cyclohexane-1-carboxamide, N-[4-(cyanomethyl)phenyl]-(1S,2S,5R)-2-isopropyl-5-methylcyclohexane-carboxamide, N-4-methoxyphenyl-(1S,2S,5R)-2-isopropyl-5-methylcyclohexanecarboxamide, N-ethyl-(1S,2S,5R)-2-isopropyl-5-methylcyclohexanecarboxamide, N-tert-butyl-(1S,2S,5R)-2-isopropyl-5-methylcyclohexanecarboxamide, ethyl (2-isopropyl-5-methylcyclohexane-1-carbonyl)glycinate, and mixtures thereof.

10. The method according to claim 7, wherein the liquid composition is an oral care composition.

11. The method according to claim 1, wherein R of the compound of formula (I) is selected from the group consisting of $C_4$-$C_5$ branched alkyl and alkenyl.

12. The method according to claim 1, wherein R of the compound of formula (I) is selected from the group consisting of $C_3$-$C_4$ branched alkyl comprising one S atom.

* * * * *